US00PP21158P3

(12) United States Plant Patent
Maillard et al.

(10) Patent No.: US PP21,158 P3
(45) Date of Patent: Jul. 13, 2010

(54) PEACH TREE NAMED 'SWEETMOON'

(50) Latin Name: *Prunus persica*
Varietal Denomination: Sweetmoon

(75) Inventors: Arsene Maillard, Elne (FR); Laurence Maillard, Elne (FR)

(73) Assignee: S.A.R.L. Agro Selection Fruits, Elne (FR)

( * ) Notice: Subject to any disclaimer, the term of this patent is extended or adjusted under 35 U.S.C. 154(b) by 0 days.

(21) Appl. No.: 12/382,125

(22) Filed: Mar. 9, 2009

(65) Prior Publication Data

US 2009/0235413 P1 Sep. 17, 2009

(30) Foreign Application Priority Data

Mar. 17, 2008 (QZ) ..... PBR 2008/0586

(51) Int. Cl.
*A01H 5/00* (2006.01)

(52) U.S. Cl. ..... Plt./195

(58) Field of Classification Search ..... Plt./195
See application file for complete search history.

*Primary Examiner*—Annette H Para
(74) *Attorney, Agent, or Firm*—Westerman, Hattori, Daniels & Adrian, LLP

(57) ABSTRACT

A new and distinct variety of peach tree, denominated 'Sweetmoon', has fruits of very long shelf life without alteration before and after harvesting, a semi-sweet white flesh of high eating quality and an attractive red skin. Fruits can be consumed crunchy or melting.

3 Drawing Sheets

Botanical classification: *Prunus persica.*
Variety denomination: 'Sweetmoon'.

BACKGROUND OF THE NEW VARIETY

The present invention relates to a new and distinct variety of peach tree, *Prunus persica* which has been given the variety denomination 'Sweetmoon'. This new tree produces fruit with a long shelf life without alteration both on the tree after growth completion and after harvesting, very good eating quality, clingstone white flesh fruit for fresh market in August in the Pyrénées-Orientales departement, France. Contrast is made to 'Zaitabo' Big Top® (non-patented) yellow nectarine tree, 'Merdame' (Elegant Lady®) (U.S. Plant Pat. No. 4,399) peach tree, standard varieties, for reliable description. 'Sweetmoon' is a promising candidate for commercial success in that it has very attractive fruits with very long shelf life without alteration before after harvesting.

ORIGIN OF THE VARIETY

The 'Sweetmoon' white peach tree originated in a cultivated area of the south of France, in the Pyrénées-Orientales departement, where it was tested. The 'Sweetmoon' variety resulted from a pollinated cross between the 'Maillarbinette' (Belbinette®) (non-patented) white peach tree, which was used as the seed parent, and the 'Maillarmagie' (Magique®) (non-patented) white nectarine tree, which was used as the pollen parent. Both parents were produced as part of our breeding program.. 'Sweetmoon' was provisionally designated, tested and genetically identified by a genetic profile, under number 03.28.16 PB and was registered at the Official Catalogue of the Agriculture Ministry of the French Republic on Nov. 14, 2007 under number 1024470. It was obtained by hybridizing and propagated by grafting on a 'Franc Inra Montclar®' (non-patented) rootstock tree. It has been determined to have unique tree and fruit characteristics making it worthy for commercial fresh fruit production. There are no known effects of the standard 'Franc Inra Montclar®' (non-patented) rootstock on the scion cultivar. Asexually propagated plants remained true to the original tree and all characteristics of the tree and the fruit were transmitted. The plant was reproduced asexually by us in Elne, Pyrénées-Orientales departement, France.

SUMMARY OF THE VARIETY

The new and distinct variety of peach tree blooms in March at Perpignan in the Pyrénées-Orientales departement, France. More particularly, it approximately blooms between the 12$^{th}$ and the 20$^{th}$ of March under normal climatic conditions, generally about 1 week later than the 'Zaitabo' Big Top® (non-patented) yellow nectarine tree variety.

The first fruit of 'Sweetmoon' peach tree ripens between the end of July and the beginning of August, generally between 5 and 6 days later than the 'Merdame' (Elegant Lady®) (U.S. Plant Pat. No. 4,399) peach variety. More particularly, it approximately ripens between July 30$^{th}$ and August 10$^{th}$ under normal climatic conditions. The date of maturity varies slightly with the prevailing climatic conditions.

DESCRIPTION OF THE DRAWINGS

In the accompanying drawing, which are as nearly true as it is reasonably possible to make in a color illustration of this type.

Figure 1:
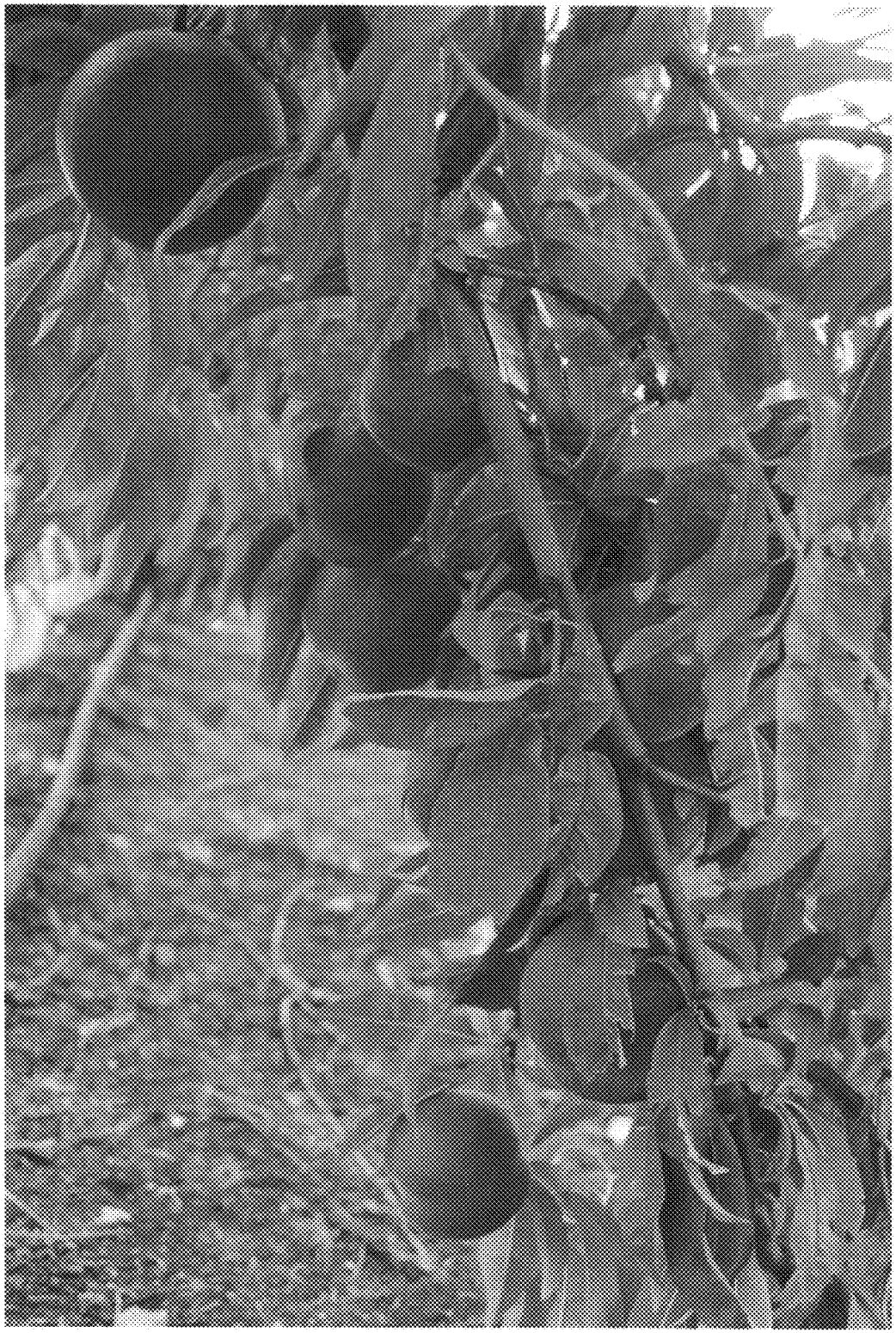
FIG. 1 is a color photograph which shows a twig bearing typical fruit specimens of the new variety, and leaves of the new variety.
Figure 2:
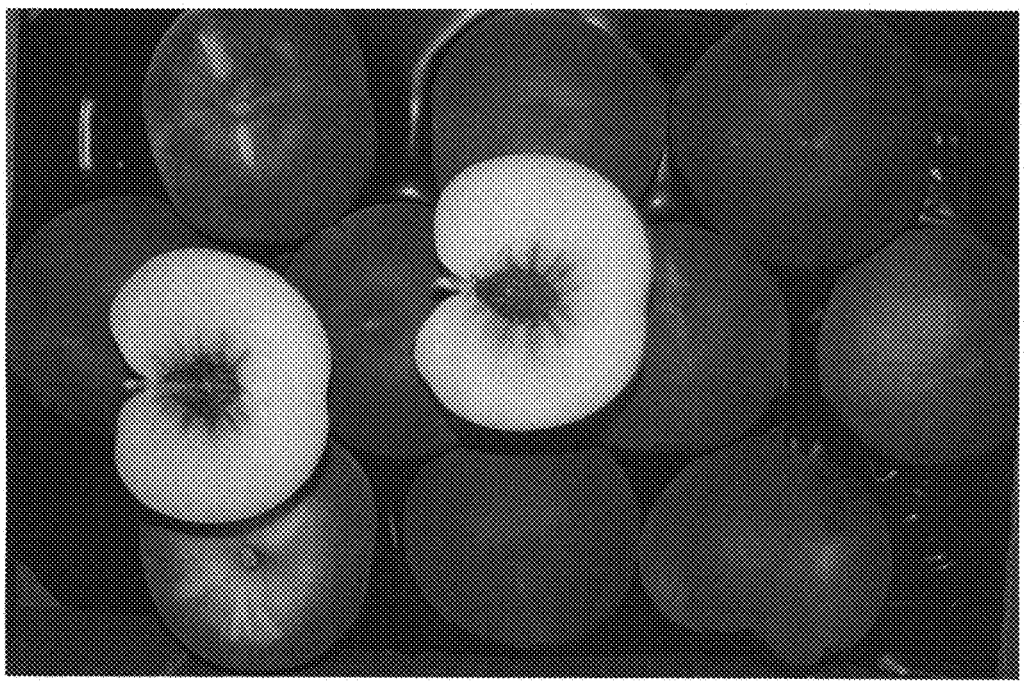
FIG. 2 is a color photograph which shows fruits of the new variety ready to be shipped, and a third fruit cut in half for depicting the fruit flesh, the pit cavity and the stone of the new variety.
Figure 3:
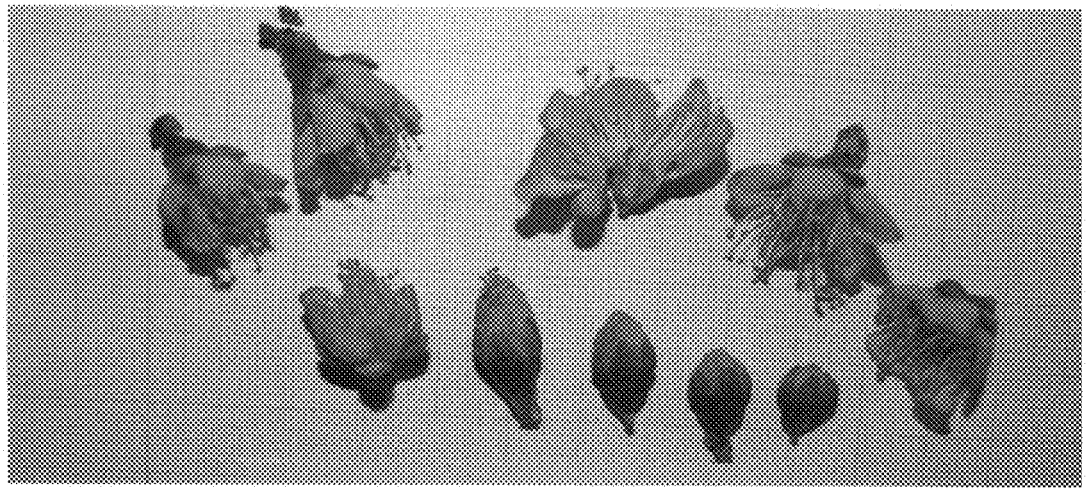
FIG. 3 is a color photograph with reverse and size views of flowers of the new variety, and, with petals removed, reproductive organs of the new variety.

Due to chemical development, processing and printing, the leaves and fruit depicted in these photographs may or may not be accurate when compared to the actual botanical specimen.

DETAILED BOTANICAL DESCRIPTION

The tree, flowers, and fruit may vary in slight detail due to variations in soil type, cultural practices, and climatic condition. The potential for commercial production of fresh fruit by 'Sweetmoon' is high, due to fruit very long shelf life without alteration before and after harvesting.

Trees are vigorous and large stature half-standing in a semi-spread to semi-upright out aspect. The anthocyanic coloration of flowering shoot is present excluding brushwood side away from sun. Flowering begins semi-late in springtime. The type of flower is non-showy with small to medium petal size. Petals are dark pink. Leaf glands are present and reniform. Time of maturity for consumption is semi-late. The fruit flesh is white and its skin is thick, with a purple red blush on a red background. The stone is medium size. Fruit taste is semi-sweet.

In comparison to its male parent, which is 'Maillarmagie' (Magique®) (non-patented), the new variety is a peach tree instead of a nectarine tree.

Differences between blooming and ripening periods of the new variety and other cultivars are provided above.

DETAILED DESCRIPTION

Referring more specifically to the pomological details of this new and distinct variety of peach tree, the following was observed on trees in their fourth growing season under the ecological conditions prevailing at the orchards located near the town of Elne, Pyrénées-Orientales departement, France. All observations have been done on rootstock cultivar. The rootstock was a 'Franc Inra Montclar®' (non-patented) tree. All major color code designations are by reference to The R.H.S. Color Chart (Fourth Edition) provided by The Royal Horticultural Society of Great Britain.

TREE

Size:

*Generally.*—Considered large as compared to other common commercial peach cultivars. The tree size the first year was approximately 280 cm. The tree was pruned during each following dormant season to a height of approximately 250 cm. Current seasons shoots growth could reach 80 cm. So the tree size from the second year (second and next years) reached a final height of 330 cm with current seasons shots length comprised.

Spread: Approximately 100 cm with a cylindrical shape. The whole orchard was oriented to a central leader organisation, with tree lines spaced of 4.0 meters and trees spaced of 1 meter in a same tree line.

Vigor: Considered averagely vigorous. The present variety grew from about 200 cm to 280 cm in height during the first growing season. For second and following seasons, the variety was pruned to an approximate height of 250 cm.

Productivity: Very Productive. Fruit set is spaced by thinning to develop the remaining fruit into the desired market sized fruit. The number of the fruit set varies with the prevailing climatic conditions and cultural practices employed during the bloom period, and is therefore not distinctive of the present variety.

Bearer: Very regular. Thinning of 1 fruit out of 3 was necessary for the tree valorisation.

Form: The 'Sweetmoon' variety has naturally a semi-spread to semi-upright shape.

Density: Considered medium dense.

Hardiness: The present tree was grown and evaluated in France. The variety appears to be hardy under the central Pyrénées-Orientales departement typical climatic conditions and was selected for its hardiness. Experimentations on different sites with winter chilling requirement comprised between 350 hours and 1200 hours showed a good behaviour of the tree in all cases. No damages were caused by ascertained temperatures as low as −12 degrees Celsius. The tree was also very resistant to frosty springtime weather.

TRUNK

Diameter: Approximately 8.5 cm in diameter when measured at a distance of approximately 30 cm above the soil level. The branching begins at 50 cm above the soil level.

Bark texture: Considered slightly rough, with folds of papery scarfskin being present.

Lenticels: Numerous lenticels are present. The lenticels range in size from approximately 5.0 millimeters to 7.0 millimeters in width, and from 1.5 millimeters to 3.0 millimeters in height.

Lenticel color: The outside of lenticels has a silver-grey color (RHS Grey 201 D to RHS Black 202 D), whereas the inside is considered brown (RHS Greyed Orange 166B).

Bark coloration: The bark has a silver-grey color a little more pronounced than lenticels outside color (RHS Grey 201 C to RHS Black 202 C).

BRANCHES

Size: Mature branches and current season shoots are considered medium to thick for the variety.

Diameter: Average as compared to other peach varieties. The current season shoots have a diameter from 5.0 to 9.0 millimeters, and observed branches have a diameter comprised between 20.0 and 30.0 millimeters.

Surface texture: Average, wood which is several years old has no furrowed appearance.

Crotch angles: Primary branches are considered variable, but the crotch angles are generally between 50 degrees and 70 degrees from the horizontal axis. This particular characteristic is not considered distinctive of the variety, however.

Current season shoots:

*Surface texture.*—Substantially glabrous.

Internode length: Generally 24.0 millimeters to 34.0 millimeters.

Color of mature branches: Medium brown (RHS Grey Brown 199 A).

Current seasons shoots:

*Color.*—The color of new shoot tips is considered a light green (RHS Green 143 C to D) on lower part of new shoot tips, whereas the upper part is colored in more or less brown-red (varying from RHS Greyed Red 182 B to C).

LEAVES

Size: Considered medium to large for the species. Leaf measurements have been taken from vigorous, upright, current-season growth at approximately mid-shoot. The ratio leaf length/leaf width ranges between 3.8 and 4.

Leaf length: Approximately 165.0 to 183.0 millimeters with leaf petiole.

Leaf width: Approximately 40.0 to 49.0 millimeters.

Leaf base shape: Concave.

Leaf form: Lanceolate.

Leaf tip form: Acuminate and small.

Leaf color:

*Upper leaf surface.*—Dark Green (RHS Green 137 A).

*Lower surface.*—Medium Green (RHS Green 137 B to 137 C).

Leaf texture: Smooth and glabrous.

Leaf venation: Pinnately veined.

Mid-vein:

*Color.*—Light green with a cream touch (RHS Yellow Green 145 D).

Leaf margins: Slightly undulating.

Form: Considered slightly dentate.

Uniformity: Leaves are isolated or grouped by 2 or 3. In this last case, it is found one leaf of normal size with one or two smaller leaves (size-reduction of 50% and more).

Leaf petioles:

*Size.*—Considered small.

*Length.*—About 9.0 mm.

*Diameter.*—About 1.7 mm.

*Color.*—Light green shading to cream-white (RHS Yellow Green 145 B to C).

Leaf glands:

*Size.*—Considered small. Their length is about 1.2 millimeters.

*Number.*—Generally 2 and occasionally 4 glands per leaf.

*Type.*—Reniform.

*Color.*—On young leaves, leaf glands color is considered a pale green (RHS Green 145 B). On older leaves, leaf glands color turn to a dark brown (RHS Grey Brown 199 A to 199 B).

Leaf stipules:

*Generally.*—No leaf stipules were observed. But as seen in the characteristic relative to the leaves uniformity, it is possible to find leaves by groups of 2 or 3, with a normal-size leaf and smaller ones.

FLOWERS

Flower buds:

*Generally.*—At pre-floral stage of development, the floral buds are conic in form with a round tip. Their form is evolving until blooming, with variables dimensions. Just before blooming, floral buds are approximately 7.0 millimeters wide and approximately 16.0 millimeters long.

Flower buds:

*Color.*—This characteristic is dependent upon the proximity to bloom. At pre-floral stage of development, the bottom of the flowers buds, formed by the sepals, is of purple-brown color (RHS Greyed Purple 183 A); the corolla, formed by the petals, is generally of pink color (RHS Red Purple 60 D). Petals color shows an evolution until the end of flowering. The buds are considered hardy under typical central Pyrénées-Orientales departement climatic conditions.

Hardiness: No winter injury was noted during the last several years of evaluation in the central Pyrénées-Orientales departement, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

Date of bloom: Generally March. The first bloom was observed on Mar. 11, 2004.

Blooming time: Considered semi-late season in relative comparison to other commercial peach cultivars grown in the Pyrénées-Orientales departement, France. The date of full bloom is observed on March. The date of bloom varies slightly with climatic conditions and cultural practices. Thus the first full bloom was observed approximately on Mar. 16, 2004.

Duration of bloom: Approximately 11 days. This characteristic varies slightly with the prevailing climatic conditions.

Flower type: The variety is considered to have a non-showy type flower.

Flower size: Considered small to medium. Flower diameter at full bloom is approximately between 20.0 and 25.0 millimeters.

Bloom quantity: Considered abundant, approximately 45 flowers per meter.

Flower bud frequency: Generally 2 flower buds appear per node, occasionally 1.

Petal size:

*Generally.*—Considered small for the species.

Length: Generally about 12.0 millimeters.

Width: Generally about 10.0 millimeters.

Petal form: Elongated with a round-shaped apex.

Petal count: Nearly always 5.

Petal texture: Smooth and glabrous.

Petal color: Dark Pink (RHS Red Purple 61 C to D) when young, slightly darkening with advancing senescence.

Fragrance: Generally slight.

Petal claw:

*Form.*—The claw is considered to have a conic form with a slightly rounded extremity.

*Length.*—Approximately 6.0 to 8.0 millimeters.

*Width.*—Approximately 4.0 to 5.0 millimeters.

Petal margins: Generally very slightly undulated.

Petal apex:

*Generally.*—The petal apices are generally dome-shaped.

Flower pedicel:

*Length.*—Considered small and having an average length of approximately 2.0 to 3.0 millimeters.

*Diameter.*—Considered average, approximately 2.0 millimeters.

*Color.*—A medium brown (RHS Grey Brown N199 C to D).

Floral nectaries:

*Color.*—A green yellow (varying from RHS Yellow 13 A to B to RHS Yellow Green 150 A to B).

Calyx:

*Internal surface texture.*—Glabrous.

*Color.*—The outer surface of the calyx is considered of Purple-brown (RHS Greyed Purple 183 A) color.

Sepals:

*Surface texture.*—The outer surface has a short, fine pubescent texture.

*Size.*—Small.

*Color.*—Purple-brown (RHS Greyed Purple 183 A).

Average number of stamens per flower: Approximately 45 stamens per flower.

Anthers:

*Generally.*—Small in length.

*Color.*—Red to orange-red color (approximately RHS Greyed Purple 178 A). Anthers are becoming yellow at maturity.

Pollen production: Pollen is abundant, and has a yellow color (Approximately RHS Yellow Orange 17 B to C). The present variety is considered self fruitful (self-pollinating).

Filaments:

*Size.*—Variable in length, approximately 10.0 to 15.0 millimeters in length. Filaments length is generally equal to the pistil's length and superior to petals length.

Color: Considered light pink (approximately RHS Red Purple 62 C to D) to pink (RHS Red Purple 73 A to B).

Pistil:

*Number.*—Usually 1.

*Generally.*—Average in size.

*Length.*—Approximately 15.0 to 20.0 millimeters including the ovary; Generally equal or slightly superior to filaments length.

*Color.*—Considered a very pale green (varying from RHS Yellow Green 150 D to RHS Yellow Green 151 D).

*Surface texture.*—Pubescent, particularly around the ovary.

FRUIT

Maturity when described: Very firm ripe condition (shipping ripe).

Date of first picking: Jul. 25, 2005.

Date of last picking: Aug. 6, 2005. The date of harvest varies slightly with the prevailing climatic conditions. The 'Sweetmoon' variety has a semi-late date of picking, and a grouped maturity: only 2 harvests in approximately 12 days are generally necessary.

Size:

*Generally.*—Considered large to very large, and homogeneous in size.

Average cheek diameter: Approximately 77.0 to 80.0 millimeters.

Average axial diameter: Approximately 69.0 to 76.0 millimeters.

Typical weight: Generally around 250.0 grams. This characteristic is highly dependent upon the prevailing cultural practices, and therefore is not particularly distinctive of the variety.

Fruit form:

*Generally.*—Round. The fruit is generally uniform in symmetry, viewed from pistil end.

Fruit suture: Wide-mouthed and slightly marked, extending from the base to the apex. No apparent callousing or stitching exists along the suture line.

Suture:

*Color.*—The suture has generally a color similar to the whole fruit color, a purple red (RHS Red Purple 59 A) on a red background (RHS Red 46 A).

Ventral surface:

*Form.*—Smooth.

Apex: Non-prominent, depressed, very small.

Base: Slightly wide-mouthed, shallow.

Stem cavity: Average depth of the stem cavity is about 1.2 cm. Average width is about 2.0 cm.

Fruit skin:

*Thickness.*—Considered very thick and strong, and tenacious to moderately tenacious to the flesh depending on stage of maturity.

*Texture.*—Slightly pubescent.

*Taste.*—Semi-sweet.

*Tendency to crack.*—None observed.

Color:

*Blush color.*—This blush color is an homogenous and luminous purple red (RHS Red Purple 59 A). The red blush covers 80% to 90% of the fruit skin surface. The percentage of the blush on the fruit skin surface can vary, and is generally dependant upon the prevailing conditions under which the fruit was grown.

*Ground color.*—The ground color appears on up to 20% of the fruit skin surface, and is considered red (RHS Red 46 A). A slight cream coloration (RHS Yellow Green Group 154 D) can appear around the stem, on a very small surface (no more than few square millimetres).

Fruit stem: Medium in length, approximately 7.0 millimeters.

Diameter: Approximately 3.0 millimeters.

Color: Pale green (RHS Yellow Green 145 A to 145 B).

Flesh:

*Ripens.*—Very evenly, homogenously, slowly, long shelf-life.

*Texture.*—Very firm, very dense, crunchy, melting, juicy at harvest maturity stage.

*Fibers.*—Generally not fibrous.

*Aroma.*—Pronounced.

*Eating quality.*—Considered very good and aromatic.

*Flavor.*—Considered semi-sweet. The Brix is superior to 13 and acidity comprised between 6 and 9 meq/100 ml. The flavor is considered aromatic.

*Juice.*—Very juicy at complete maturity.

*Brix.*—Generally superior to 13.0 degrees. This characteristic varies slightly with the number of fruit per tree; prevailing cultural practices; and the surrounding climatic conditions.

*Flesh color.*—White flesh (RHS White Group 155 C) with a very intense and star-shaped red pigmentation (RHS Red Purple 61 A to C) into the stone cavity and up to 10 millimeters around the stone cavity.

STONE

Type: Clingstone.

Size: Considered medium for the variety. The stone size varies significantly depending upon the tree vigor, crop load and prevailing growing conditions.

Length: Approximately 34.0 to 38.0 millimeters.

Width: Approximately 26.0 to 28.0 millimeters.

Diameter: Approximately 18.0 to 19.0 millimeters.

Form: Elliptic.

Base: Generally straight.

Apex:

*Shape.*—The stone apex is short and acuminate.

Stone cavity: Considered medium size, with an elliptic-form and dimensions corresponding to the stone's dimensions.

Stone surface:

*Surface texture.*—The pit is transversely furrowed on its entire surface. Furrows are more pronounced toward the apex. The stone is pitted toward the base. Relief is prominent generally and present basally.

*Ridges.*—The surface texture is generally characterized by more prominent ridges along the ventral edges and is more prominent at the apical tip.

Ventral edge:

*Width.*—Considered small to medium, and having a dimension of approximately 2.0 millimeters at mid-suture.

Dorsal edge:

*Shape.*—Grooved.

Stone color: The color of the dry stone is generally considered a light orange-brown (RHS Greyed Orange 176 D) to red-brown (RHS Greyed Red 178 B).

Tendency to split: Splitting is generally absent, depending on climatic conditions between blooming period and stone hardening.

Kernel:

*Size.*—The kernel is considered medium.

*Length.*—Approximately 20.0 millimeters.

*Width.*—Approximately 12.0 millimeters.

*Thickness.*—Approximately between 3.0 and 4.0 millimeters.

*Form.*—Considered oblate and elliptic.

*Pellicle.*—Pubescent.

*Color.*—The kernel skin is a light orange-brown (RHS Greyed Orange 167 C) with darker streaks (RHS Greyed Orange 166 C). The almond is cream-white (RHS Orange White 159 D). The kernel and its embryo are mature at the time of fruit maturity.

Use: The subject variety 'Sweetmoon' is considered to be a peach tree of the semi-late season of maturity, and which produces fruits that are considered firm, attractively colored. Fruits have a semi-sweet taste and are excellent for uncooked consumption, crunchy or melting when at full maturity. Due to their flesh quality, firmness and density, they can also be commercialized as $4^{th}$ range product (packed fruit or fruit in bags for example). And they are also useful for both local and very long distance shipping.

Keeping quality: Good to very good. Fruits have a slow maturation. Storage should be possible at 2.0 degree Celsius for more than one month.

Shipping quality: Considered good. The fruit of the new peach variety showed minimal bruising of the flesh or skin damage after being subjected to normal harvesting and packing procedures. Its resistance to handling during harvest and packing and its long shelf life without alteration after harvest permit 2 weeks to 3 weeks-shipping at 2 degrees Celsius.

Resistance to insects and disease: No particular susceptibilities were noted. The present variety is not very sensitive to powdery mildew, or conservation diseases and decay due to its thick and strong skin.

Although the new variety of peach tree possesses the described characteristics when grown under the ecological conditions prevailing near Elne, Pyrénées-Orientales departement, France, it should be understood that variations of the usual magnitude and characteristics incident to changes in growing conditions, fertilization, pruning, pest control and horticultural management are to be expected.

I claim:

1. A new and distinct variety of peach tree as illustrated and described, characterized by fruits of very long shelf life without alteration before and after harvesting, and with a semi-sweet white flesh of high eating quality and an attractive skin, with a very high percentage of red blush.

* * * * *